(12) United States Patent
Reyes et al.

(10) Patent No.: US 10,543,302 B2
(45) Date of Patent: Jan. 28, 2020

(54) MAP MEASUREMENT ON VAD PATIENTS WITH LOW PULSATILITY

(71) Applicant: HeartWare, Inc., Miami Lakes, FL (US)

(72) Inventors: Carlos Reyes, Davie, FL (US); Fernando Casas, Miami Lakes, FL (US)

(73) Assignee: HeartWare, Inc., Miami Lakes, FL (US)

( * ) Notice: Subject to any disclaimer, the term of this patent is extended or adjusted under 35 U.S.C. 154(b) by 70 days.

(21) Appl. No.: 15/678,555

(22) Filed: Aug. 16, 2017

(65) Prior Publication Data
US 2019/0054222 A1 Feb. 21, 2019

(51) Int. Cl.
*A61M 1/10* (2006.01)
*A61M 1/12* (2006.01)

(52) U.S. Cl.
CPC .......... *A61M 1/1086* (2013.01); *A61M 1/101* (2013.01); *A61M 1/1005* (2014.02); *A61M 1/122* (2014.02); *A61M 2205/3334* (2013.01); *A61M 2205/3365* (2013.01); *A61M 2205/50* (2013.01); *A61M 2230/30* (2013.01)

(58) Field of Classification Search
CPC .. A61M 1/1086; A61M 1/1005; A61M 1/122; A61M 1/101; A61M 2205/3334; A61M 2205/3365; A61M 2205/50; A61M 2205/30
See application file for complete search history.

(56) References Cited

U.S. PATENT DOCUMENTS

| | | |
|---|---|---|
| 6,527,699 B1 | 3/2003 | Goldowsky |
| 6,688,861 B2 | 2/2004 | Wampler |
| 7,575,423 B2 | 8/2009 | Wampler |
| 7,976,271 B2 | 7/2011 | LaRose et al. |
| 8,419,609 B2 | 4/2013 | Shambaugh, Jr. et al. |

(Continued)

FOREIGN PATENT DOCUMENTS

| | | |
|---|---|---|
| WO | 2014179271 A2 | 11/2014 |
| WO | 2016089693 A1 | 6/2016 |

OTHER PUBLICATIONS

International Search Report and Written Opinion dated Apr. 19, 2018, for corresponding International Application No. PCT/US2017/047118; International Filing Date: Aug. 16, 2017 consisting of 15-pages.

*Primary Examiner* — Amanda K Hulbert
(74) *Attorney, Agent, or Firm* — Christopher & Weisberg, P.A.

(57) ABSTRACT

A method of operating an implantable blood pump implanted within a heart of a patient comprising measuring at least one from the group consisting of a current drawn by the implantable blood pump and a blood flow from the implantable blood pump during operation; correlating the at least one from the group consisting the current and the blood flow to a systolic arterial pressure and a diastolic arterial pressure; and adjusting a speed of an impeller of the implantable blood pump relative to a predetermined speed to correspond to an increase the at least one from the group consisting the current during a systolic phase of a cardiac cycle and a decrease in the at least one from the group consisting the current and the blood flow during a diastolic phase of the cardiac cycle.

17 Claims, 5 Drawing Sheets

(56) References Cited

U.S. PATENT DOCUMENTS

| | | |
|---|---|---|
| 2011/0160518 A1 | 6/2011 | Zafirelis et al. |
| 2016/0000983 A1 | 1/2016 | Mohl et al. |
| 2016/0045654 A1 | 2/2016 | Connor |
| 2016/0151553 A1 | 6/2016 | Bonde |
| 2016/0228628 A1* | 8/2016 | Medvedev .......... A61M 1/1086 |
| 2017/0049945 A1 | 2/2017 | Halvorsen et al. |

* cited by examiner

MAP MEASUREMENT ON VAD PATIENTS WITH LOW PULSATILITY

CROSS-REFERENCE TO RELATED APPLICATION n/a

STATEMENT REGARDING FEDERALLY SPONSORED RESEARCH OR DEVELOPMENT n/a

TECHNICAL FIELD

This disclosure relates a method and a system for operating an implantable blood pump and measuring a blood pressure of a patient with the implantable blood pump.

BACKGROUND

Implantable blood pumps provide mechanical circulatory support to patients having a weakened or otherwise compromised heart. Generally, implantable blood pumps include a pumping mechanism to move blood from the heart to the rest of the body. In operation, the blood pump draws blood from a source, such as the right ventricle, left ventricle, right atrium, or left atrium of the patient's heart and impels the blood into an artery, such as the patient's ascending aorta or peripheral artery.

Patients requiring an implantable blood pump typically have underlying heart issues, such as low pulsatility. Generally, pulsatility reflects the heart's contractility and stretch, as well as the volume of blood moved by the heart. As a result of low pulsatility, medical complications can arise, including aortic leaflet fusion, ventricular and systematic thrombosis, unclear perfusion of the peripheral microcirculatory bed due to the issues related to blood flow, and the like.

Typically, Mean Arterial Pressure ("MAP") is determined in an effort to manage and prevent medical complications. MAP is generally defined as the average pressure in a patient's arteries during one cardiac cycle and may be obtained using a patient's diastolic blood pressure and systolic blood pressure. Unfortunately, it is often difficult to determine MAP in patients having low pulsatility, such as those having the implantable blood pump, because a signal strength of the patient's pulse pressure may be lower than that which is needed for an instrument to detect the patient's pressure limits, such as the diastolic blood pressure and the systolic blood pressure. For example, traditional commercial blood pressure cuffs may be unable to detect the patient's pulse pressure because the pulse signal strength is not strong enough to provide a stable blood pressure reading. As a result, the patient may be exposed to medical complications that may have otherwise been managed or prevented through accurate blood pressure measurements.

SUMMARY

A method of operating of a blood pump implanted within a heart includes measuring at least one from the group consisting of a current drawn by the implantable blood pump and a blood flow from the implantable blood pump during operation, correlating the at least one from the group consisting of the current and the blood flow to a systolic arterial pressure and a diastolic arterial pressure, and adjusting a speed of an impeller of the implantable blood pump relative to a predetermined speed to correspond to an increase in the at least one from the group consisting of the current and the blood flow during a systolic phase of a cardiac cycle and a decrease in the at least one from the group consisting of the current and the blood flow during a diastolic phase of the cardiac cycle.

In one aspect of this embodiment, the method includes obtaining and recording a mean arterial pressure of the patient.

In one aspect of this embodiment, the method includes adjusting the speed of the impeller based upon the average blood flow value.

In one aspect of this embodiment, the set speed of the impeller is a range of 1800 rotations per minute to 4000 rotations per minute.

In one aspect of this embodiment, adjusting the speed of the impeller includes increasing the speed of the impeller relative to the predetermined speed by at least 20 percent during the systolic phase.

In one aspect of this embodiment, adjusting the speed of the impeller includes decreasing the speed of the impeller relative to the predetermined speed by at least 20 percent during the diastolic phase.

In one aspect of this embodiment, the speed of the impeller is automatically increased relative to the predetermined speed by a controller.

In one aspect of this embodiment, the speed of the impeller gradually increases relative to the predetermined speed between a pair of adjacent systolic phases.

In one aspect of this embodiment, the increase in speed of the impeller between a pair of adjacent systolic phases is a step-up.

In one aspect of this embodiment, the increase in speed of the impeller between a pair of adjacent systolic phases is a ramp-up.

In another embodiment, an implantable blood pump system includes a blood pump, an impeller in communication with the blood pump, a controller in communication with the blood pump, the controller configured to measure a current drawn by the blood pump and a blood flow from the blood pump during operation, correlate the current to a systolic arterial pressure and a diastolic arterial pressure, and adjust a speed of the impeller relative to a predetermined speed and the blood flow to correspond to an increase in the current correlated to the systolic arterial pressure and a decrease in the current correlated to the diastolic arterial pressure.

In one aspect of this embodiment, the controller may be configured to graphically record the current drawn by the blood pump before and after the speed of the impeller is adjusted relative to the predetermined speed.

In one aspect of this embodiment, the controller is configured to record a mean arterial pressure.

In one aspect of this embodiment, the controller is configured to automatically adjust the speed of the impeller relative to the predetermined speed.

In one aspect of this embodiment, the controller is configured to initiate a step-up, the step-up including an increase in the speed of the impeller between a pair of adjacent systolic phases.

In one aspect of this embodiment, the controller is configured to initiate a ramp-up.

In one aspect of this embodiment, the controller maintains the predetermined speed of the impeller in a range of 1800 rotations per minute to 4000 rotations per minute.

In one aspect of this embodiment, the controller is configured to at least one of the group consisting of measure the blood flow and estimate the blood flow over a period of time to obtain an average blood flow value and adjust the speed of the impeller based upon the average blood flow value.

In one aspect of this embodiment, the controller is configured to gradually increase the speed of the impeller between a first systolic phase and a second systolic phase, the first systolic phase and the second systolic phase adjacent to each other.

In another embodiment, a method of measuring a blood pressure of a patient having an implantable blood pump includes measuring a current drawn by the implantable blood pump during operation; measuring an average blood flow value from the implantable blood pump during operation; correlating the current to a systolic arterial pressure and a diastolic arterial pressure of a patient; adjusting a speed of an impeller of the implantable blood pump based upon the average blood flow value relative to a predetermined speed to correspond to an increase in the current, the increase corresponding to the systolic arterial pressure of a patient, and a decrease in the current, the decrease corresponding to the diastolic arterial pressure of the patient; and recording a mean arterial pressure in response to the adjustment of the speed of the impeller relative to the predetermined speed and the average blood flow value.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Before describing in detail exemplary embodiments that are in accordance with the disclosure, it is noted that components have been represented where appropriate by conventional symbols in drawings, showing only those specific details that are pertinent to understanding this embodiments of the disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Figure 1:
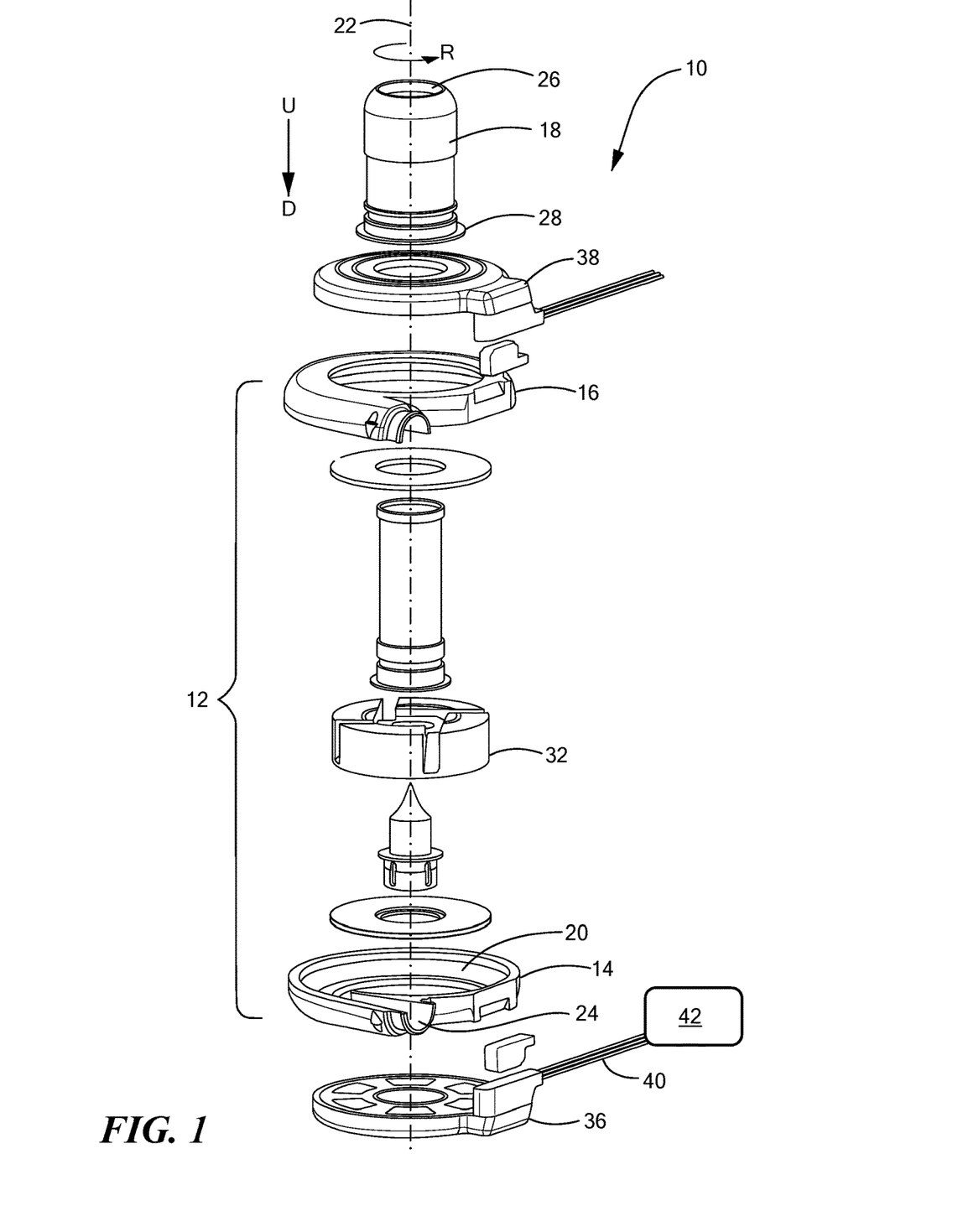
FIG. 1 is an exploded view of an exemplary blood pump constructed in accordance of the principles of the present application.

Referring now to the drawing figures in which like reference designators refer to like elements, there is shown in FIG. 1 an exemplary blood pump constructed in accordance with the principles of the present application and designated generally "10." The blood pump 10 may be the blood pump sold under the designation HVAD® by HeartWare, Inc., assignee of the present application. The arrangement of components, such as the magnets, electromagnetic coils, and hydrodynamic bearings used in the exemplary blood pump 10 and variants of the same general design are described in U.S. Pat. Nos. 6,688,861; 7,575,423; 7,976,271; and 8,419,609, the disclosures of which are incorporated by reference herein. The blood pump may also be that which is sold under the designation MVAD® by HeartWare, Inc. The method and system disclosed herein, however, are not limited to a particular type of blood pump.

The blood pump 10, according to one embodiment of the disclosure, includes a housing 12 which houses the components of the blood pump 10. In one configuration, the housing 12 includes a first portion 14, a second portion 16, and an inflow cannula 18. The first portion 14 and the second portion 16 cooperatively define a volute-shaped chamber 20 having a major longitudinal axis 22 extending through the first portion 14 and inflow cannula 18. The first portion 14 and the second portion 16 define an outlet 24 in communication with chamber 20.

Figure 2:
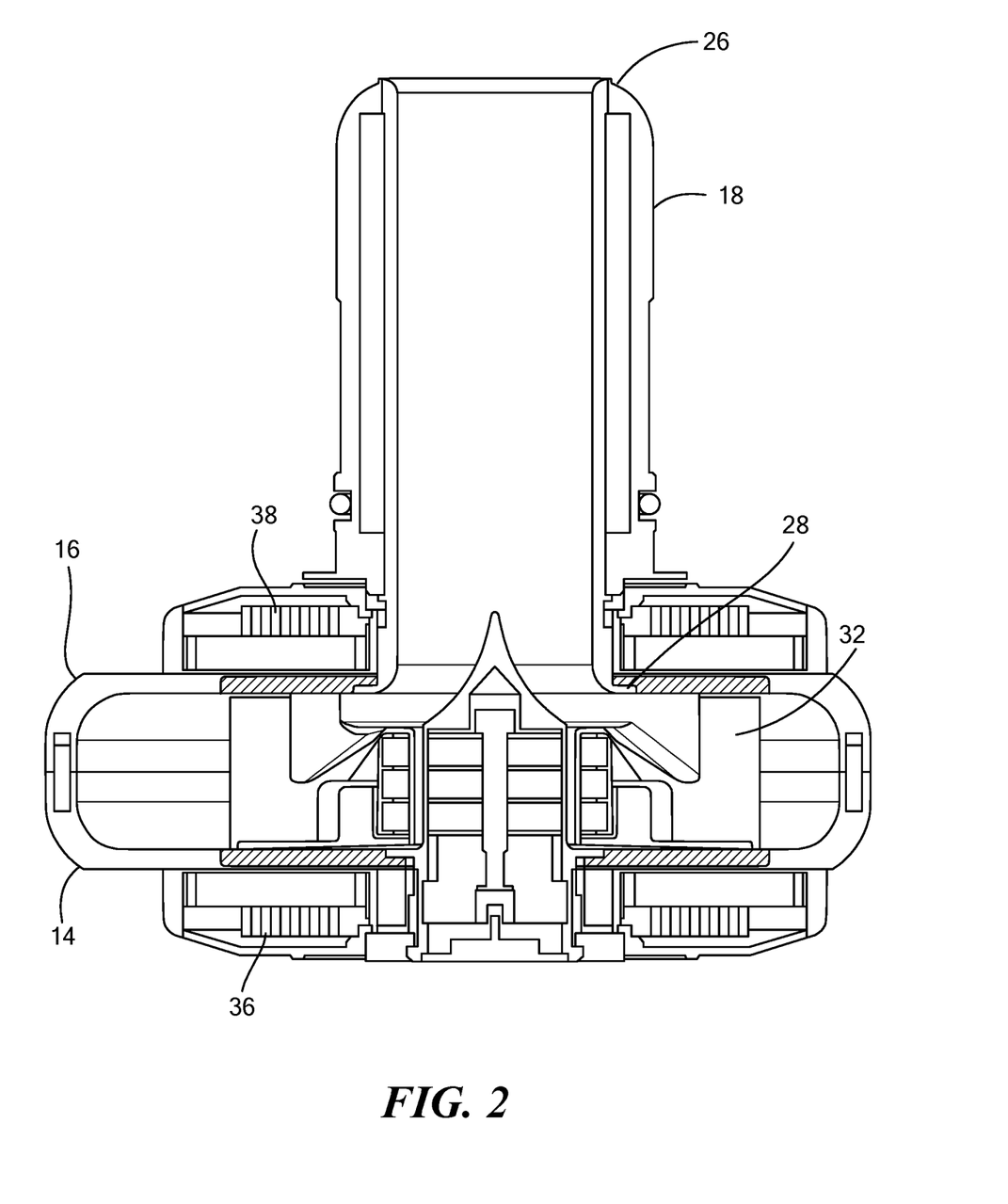
FIG. 2 is a cross-sectional view of the assembled blood pump shown in FIG. 1.

Referring now to FIGS. 1, and 2, the housing 12 defines a continuous enclosed flow path traveling through an upstream end 26 to a downstream end 28 of the inflow cannula 18, as indicated in FIG. 1 by the arrows U and D respectively. An impeller 32 is mounted within the chamber 20 for rotation about the axis 22. The impeller 32 includes a permanent magnet and flow channels for transferring blood from adjacent the center of the impeller 32 to the periphery of the impeller 32. A first stator 36 having at least two coils may be disposed within the first portion 14 such that when a current is applied to the coils, the electromagnetic forces generated by the first stator 36 rotate the impeller 32 to impel the blood. A second stator 38 may be disposed within the second portion 16 and may be configured to operate in conjunction with or independently of the first stator 36 to rotate the impeller 32.

An electrical connector 40 (FIG. 1) is provided on the first portion 14 for connecting the coils to a source of power, such as a controller 42, configured to be external to the patient. The controller 42 may include various software and hardware components for operating the blood pump 10. The source of power is not limited to the controller 42, however, as other sources of power may be used, such as a battery, a driveline, and the like. The controller 42 is arranged to apply power to the coils of the pump to create a rotating magnetic field which spins the impeller 32 around the axis 22 in a direction of rotation that is clockwise, as designated by "R," or counterclockwise. Rotation of the impeller 32 impels blood in a downstream direction D along the flow path to the outlet 24.

The controller 42 may be configured to measure the current drawn by the blood pump 10 and/or a blood flow from the blood pump 10, such as from the outlet 24, during operation. The controller 42 may also include a standard mode in which the controller 42 is configured to maintain a speed of the impeller 32 at a predetermined speed and a blood pressure mode in which the speed of the impeller 32 is adjusted to raise a patient's blood pressure in an effort to measure the patient's MAP using a blood pressure measurement device.

Figure 3:
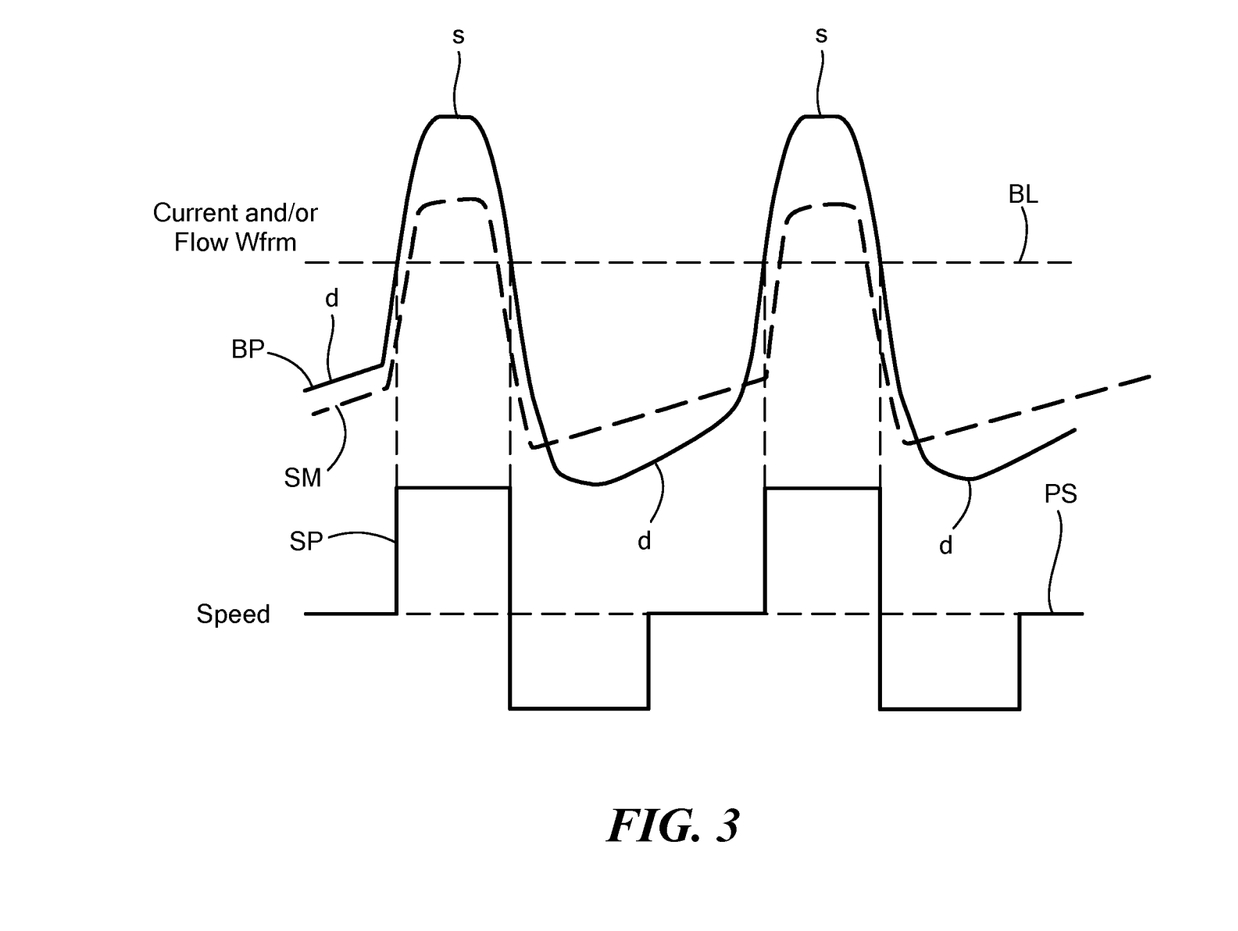
FIG. 3 is a graph depicting a current and/or a flow waveform and a speed of an impeller of the blood pump shown in FIG. 1 during a cardiac cycle of a heart.

With reference to FIG. 3, the current and/or the blood flow may be measured by the controller 42 relative to a baseline, designated as "BL." The measurement of the current may be determined using information associated with a resistance in the electrical connection and a voltage, or another measurement method. The measurement of the blood flow may be determined using the current, the speed of the impeller 32, and the viscosity of the blood, or another measurement method.

The measurement of the current and/or the blood flow may be correlated to a systolic arterial pressure and a diastolic arterial pressure of a patient having the blood pump 10 implanted in the patient's heart. Said another way, the current and the blood flow measurements of the blood pump 10 are configured to provide real-time information about the cardiac cycle of the patient's heart. FIG. 3 depicts an exemplary cardiac cycle including a systolic phase, designated as "s," and a diastolic phase, designated as "d." The amount of the current and/or the blood flow through the blood pump 10 is graphically depicted via a waveform when the controller 42 is in the standard mode, designated as "SM," and the blood pressure mode, designated as "BP."

The systolic phase may be determined as the current and/or the blood flow through the blood pump 10 is configured to increase relative to the baseline when the heart is contracting as the blood pump 10 naturally requires an increase in the current to pump the blood. The diastolic phase may be determined as the current and/or the blood flow waveform is configured to decrease when the heart transitions from the systolic phase to the diastolic phase because the blood pump 10 requires less current when the heart is relaxing and filling with the blood than that required during contracting. The cycle shown in FIG. 3 is an exemplary cycle as the amount of current and/or the blood flow through the blood pump 10 may vary between patients.

With reference still to FIG. 3, in the standard mode, the controller 42 is configured to maintain the speed of the impeller 32 at a predetermined speed, designated as "PS." In one configuration, the predetermined speed may be at least 1800 revolutions per minute, such as in a range of 1800 rotations to 4000 rotations per minute. Additional ranges are also possible in accordance with the type of blood pump and the needs of the individual patient. When the controller 42 is in the standard mode, including the impeller 23 being set to the predetermined speed, the current and/or the blood flow may not produce an amount of arterial pressure needed to measure that patient's MAP. For example, the patient may have low pulsatility, which generally includes a pulse pressure that is too low to be measured with a blood pressure device, such as a blood pressure cuff.

Figure 4:
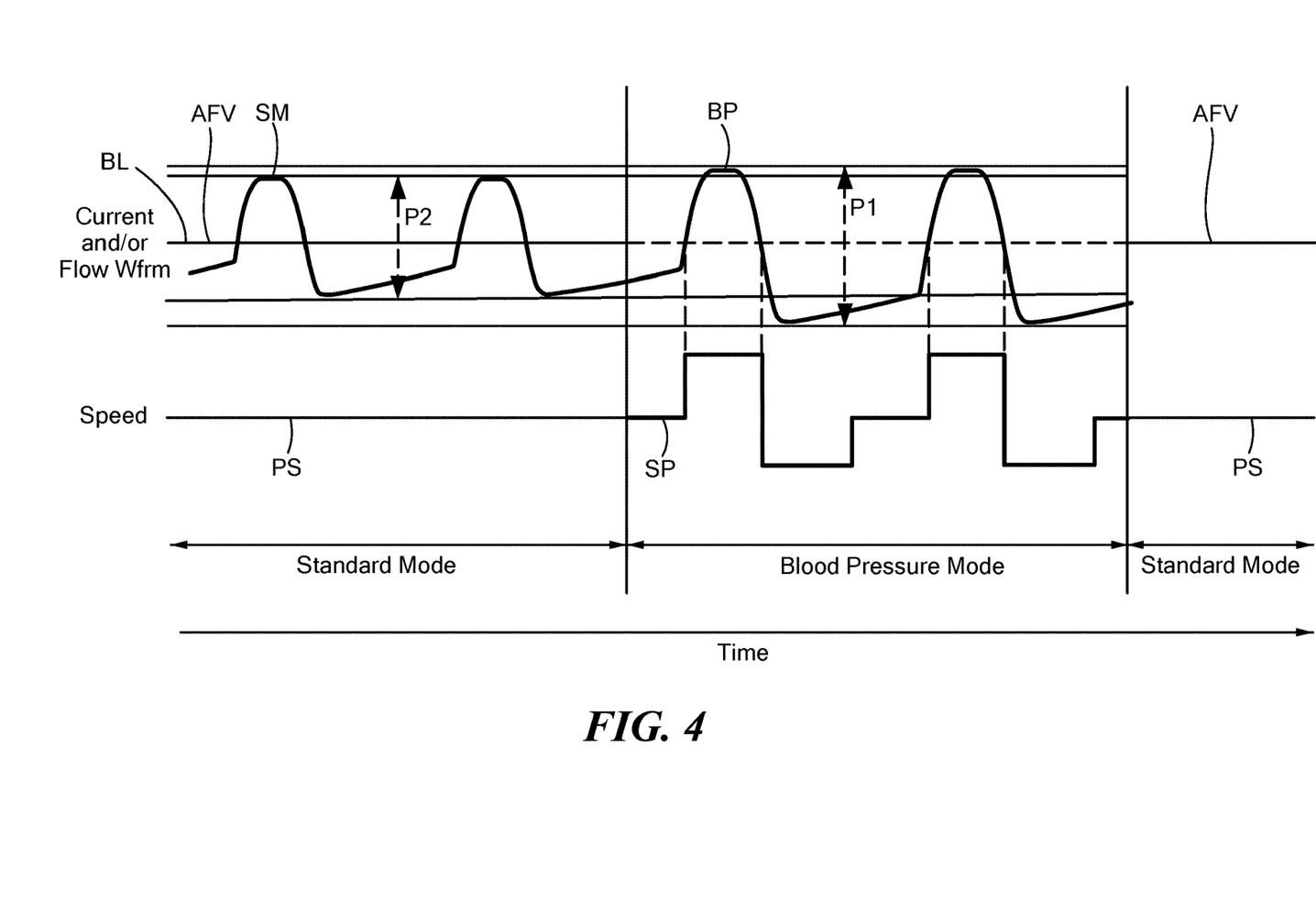
FIG. 4 is a graph depicting a controller configured to adjustment the speed of the impeller of the blood pump shown in FIG. 1 during a standard mode and a blood pressure mode.

With reference to FIGS. 3 and 4, in the blood pressure mode, the speed of the impeller 32 may be increased relative to the predetermined speed "PS," in accordance with an increase in the current and/or the blood flow during systole and may be decreased in accordance with a decrease in the current and/or blood flow during diastole, such that the speed is synchronized with the patient's cardiac cycle. The speed adjustment is configured to amplify and attenuate the arterial pressure of the patient in an effort to measure the patient's MAP using the blood pressure device.

In one configuration, the amount of the speed adjustment may be determined using information associated with the blood flow of the blood pump 10, such as an average blood flow value over time. As shown in FIG. 4, the speed of the impeller 32 may be adjusted to various speeds until the average blood flow measured before and after the blood pressure mode is equal to the average blood flow value during the blood pressure mode, designated as "AFV," so as not to affect the patient's MAP. When the average blood flow value is maintained during the blood pressure mode, the amplified arterial pressure during the speed increase may be balanced by the attenuated arterial pressure during the speed decrease so as to maintain an energy content of the arterial pressure waveform constant during the blood pressure mode. In other words, by maintaining a zero-relative change in the average blood flow value through the blood pump 10 during the standard mode compared to the blood pressure mode, the patient's mean arterial pressure will not be affected by the speed adjustment.

In order to obtain the average blood flow value, the controller 42 may be configured to measure and/or estimate the blood flow over a period of time, such as ten to twenty-minute intervals, hourly, daily, or the like. The average blood flow value may also be determined using a data-table corresponding to the individual patient or another measurement method, such as adjusting the speed of the impeller 32 to various intervals and thereafter measuring the blood flow through the blood pump 10 until the average blood flow value is maintained.

As shown in FIGS. 3 and 4, the selective adjustment of the speed of the impeller 32 is designated as "SP," and the corresponding increase and decrease in the current and/or blood flow waveform is designated as "BP." In one configuration, the decrease in speed of the impeller 32 is configured to cause the current and/or blood flow waveform in the blood pressure mode to drop below the current and/or blood flow waveform in the standard mode. The increase and the decrease in speed relative to the predetermined speed may be plus or minus 20 percent, or as otherwise established in accordance with the patient's cardiac cycle. In one configuration, as shown in FIG. 3, the increase in speed may be a step-up, which may include a relatively instantaneous increase in the speed of the impeller 32 during a diastolic phase between a pair of adjacent systolic phases. Alternatively, the controller 42 may be configured to perform a ramp-up (not shown), which is a relatively gradual increase in the speed of the impeller 32 between the pair of adjacent systolic phases.

With reference again to FIG. 4, the amplification in the arterial pressure is graphically represented by an increase in a peak length of the current and/or the blood flow waveform during the blood pressure mode, designated as P1, in comparison to a length of the peak in the standard mode, designated as P2. As shown, the current and/or the blood flow waveform and correlated arterial pressure is configured to be higher when the controller 42 is in the blood pressure mode, as a result of the speed adjustment, than that which occurs during the standard mode when the speed is predetermined. Accordingly, the patient's blood pressure may be measured in the blood pressure mode when the arterial pressure is amplified.

Figure 5:
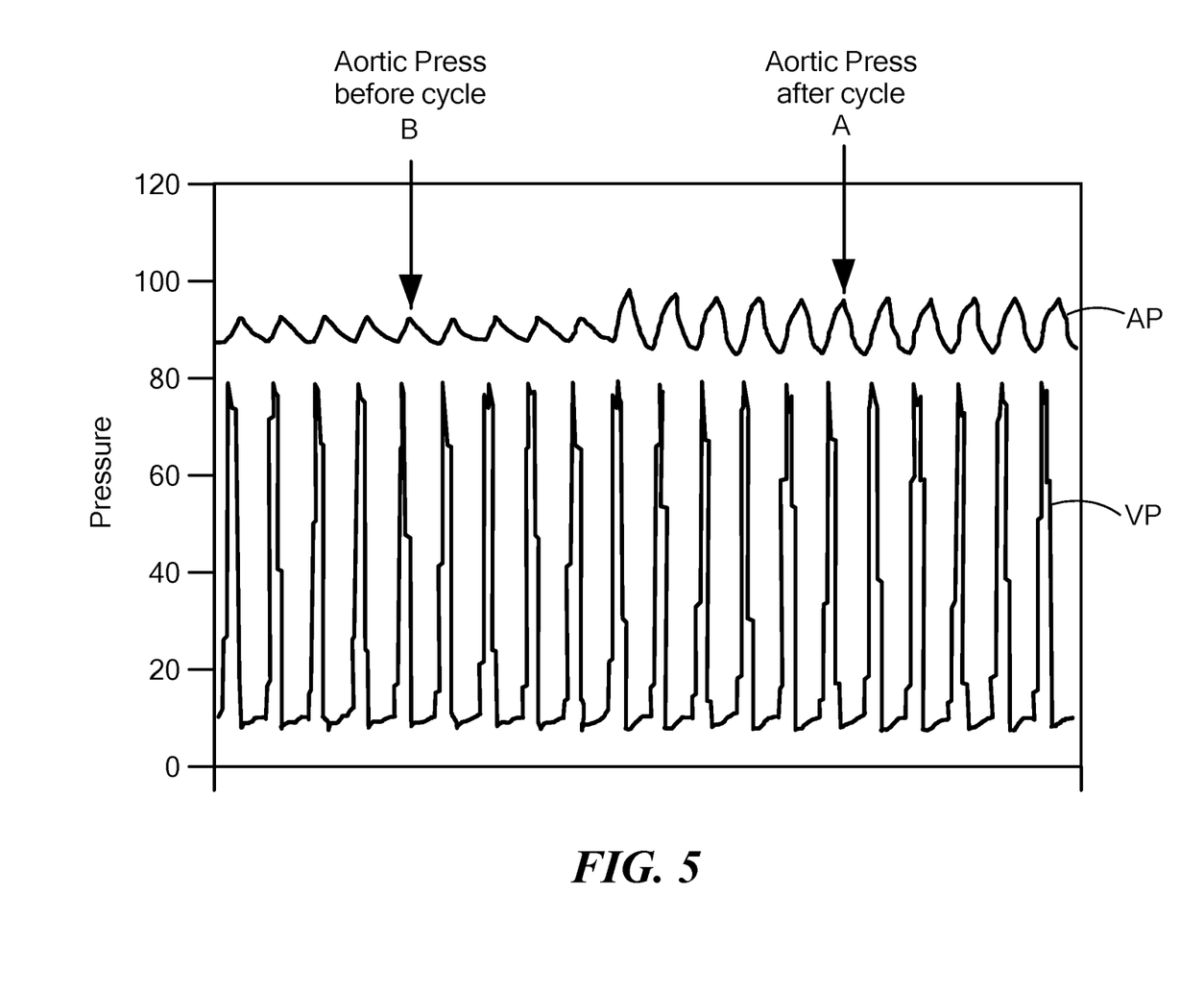
FIG. 5 is a graph depicting an aortic pressure and a ventricular pressure of the heart in a computer simulation.

With reference to FIG. 5, a graph is depicted showing an exemplary cardiac cycle in a computer simulation including an aortic pressure, designated as "AP," and a ventricular pressure, designated as "VP," before and after the speed of the impeller 23 is increased relative to the predetermined speed in an effort to raise the patient's arterial pressure such that MAP can be determined. The controller 42 may be configured to adjust the speed and record the corresponding aortic and ventricular pressures. The aortic pressure before the increase in speed is designed as "B" and is configured to be lower than the aortic pressure after the increase in speed, which is designated as "A." The ventricular pressure is configured to remain constant, regardless of the speed adjustment. The graph disclosed in FIG. 5 is not intended to be limiting as additional methods of recordation may also be used, such as line graphs, bar graphs, charts, and the like.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of operating an implantable blood pump implanted within a heart of a patient comprising:
   measuring a blood flow from the implantable blood pump during operation;
   correlating the blood flow to a systolic arterial pressure and a diastolic arterial pressure;
   measuring the blood flow over a period of time to obtain an average blood flow value;
   obtaining and recording a mean arterial pressure of the patient;
   adjusting a speed of an impeller of the implantable blood pump during a systolic-diastolic cycle relative to a predetermined speed to correspond to an increase in the blood flow during a systolic phase of the systolic-diastolic cycle and a decrease in the blood flow during a diastolic phase of systolic-diastolic cycle; and
   maintaining the patient's average blood flow and mean arterial pressure to be constant during the systolic-diastolic cycle.

2. The method of claim 1, further comprising adjusting the speed of the impeller based upon the average blood flow value.

3. The method of claim 1, wherein adjusting the speed of the impeller includes increasing the speed of the impeller relative to the predetermined speed by at least 20 percent during the systolic phase.

4. The method of claim 1, wherein adjusting the speed of the impeller includes decreasing the speed of the impeller relative to the predetermined speed by at least 20 percent during the diastolic phase.

5. The method of claim 1, wherein the speed of the impeller is automatically increased relative to the predetermined speed by a controller.

6. The method of claim 1, wherein the increase in speed of the impeller between a pair of adjacent systolic phases is a step-up.

7. The method of claim 1, wherein the increase in speed of the impeller between a pair of adjacent systolic phases is a ramp-up.

8. The method of claim 1, wherein current drawn from the implantable blood pump is measured and correlated to a systolic arterial pressure and a diastolic arterial pressure so as to adjust a speed of an impeller of the implantable blood pump relative to a predetermined speed to correspond to an increase in the current during a systolic phase of a cardiac cycle and a decrease in the current during a diastolic phase of the cardiac cycle.

9. An implantable blood pump system comprising:
   a blood pump;
   an impeller in communication with the blood pump; and
   a controller in communication with the blood pump, the controller configured to:
   measure a current drawn by the blood pump and a blood flow from the blood pump during operation;
   correlate the current to a systolic arterial pressure and a diastolic arterial pressure;
   measuring the blood flow over a period of time to obtain an average blood flow value;
   record a mean arterial pressure;
   adjust a speed of the impeller during a systolic-diastolic cycle relative to a predetermined speed and the blood flow to correspond to an increase in the current correlated to the systolic arterial pressure and a decrease in the current correlated to the diastolic arterial pressure; and
   adjust the speed of the impeller during the systolic-diastolic cycle to various speeds until the average blood flow is maintained during the speed adjustment, so as to not affect the patient's mean arterial pressure.

10. The system of claim 9, wherein the controller is configured to graphically record the current drawn by the blood pump before and after the speed of the impeller is adjusted relative to the predetermined speed and the blood flow.

11. The system of claim 9, wherein the controller is configured to automatically adjust the speed of the impeller relative to the predetermined speed.

12. The system of claim 11, wherein the controller is configured to initiate a step-up, the step-up including an increase in the speed of the impeller between a pair of adjacent systolic phases.

13. The system of claim 11, wherein the controller is configured to initiate a ramp-up.

14. The system of claim 9, wherein the controller maintains the predetermined speed of the impeller in a range of 1800 rotations per minute to 4000 rotations per minute.

15. The system of claim 9, wherein the controller is configured to at least one from the group consisting of measure the blood flow and estimate the blood flow over a period of time to obtain an average blood flow value and adjust the speed of the impeller based upon the average blood flow value.

16. The system of claim 9, wherein the controller is configured to gradually increase the speed of the impeller between a first systolic phase and a second systolic phase, the first systolic phase and the second systolic phase adjacent to each other.

17. A method of measuring a blood pressure of a patient having an implantable blood pump comprising:
   measuring a current drawn by the implantable blood pump during operation;
   measuring an average blood flow value from the implantable blood pump during operation;

correlating the current to a systolic arterial pressure and a diastolic arterial pressure of a patient;

adjusting a speed of an impeller of the implantable blood pump based upon the average blood flow value relative to a predetermined speed to correspond to an increase in the current, the increase corresponding to the systolic arterial pressure of a patient, and a decrease in the current, the decrease corresponding to the diastolic arterial pressure of the patient; and recording a mean arterial pressure in response to the adjustment of the speed of the impeller relative to the predetermined speed and the average blood flow value.

\* \* \* \* \*